US012557849B2

(12) United States Patent
Hou et al.

(10) Patent No.: US 12,557,849 B2
(45) Date of Patent: Feb. 24, 2026

(54) ELECTRONIC CIGARETTE WITH SUCTION RESISTANCE ADJUSTING FUNCTION

(71) Applicant: SHENZHEN HANQINGDA TECHNOLOGY CO., LTD., Guangdong (CN)

(72) Inventors: Shoushan Hou, Guangdong (CN); Qianfeng Zhao, Guangdong (CN); Shihua Li, Guangdong (CN)

(73) Assignee: SHENZHEN HANQINGDA TECHNOLOGY CO., LTD., Shenzhen (CN)

( * ) Notice: Subject to any disclaimer, the term of this patent is extended or adjusted under 35 U.S.C. 154(b) by 425 days.

(21) Appl. No.: 18/265,126

(22) PCT Filed: Dec. 21, 2022

(86) PCT No.: PCT/CN2022/140530
§ 371 (c)(1),
(2) Date: Jun. 2, 2023

(87) PCT Pub. No.: WO2023/202124
PCT Pub. Date: Oct. 26, 2023

(65) Prior Publication Data
US 2024/0398021 A1 Dec. 5, 2024

(30) Foreign Application Priority Data
Apr. 19, 2022 (CN) .......................... 202220912044.1

(51) Int. Cl.
*A24F 40/485* (2020.01)
*A61M 15/06* (2006.01)
*A61M 15/00* (2006.01)

(52) U.S. Cl.
CPC ......... *A24F 40/485* (2020.01); *A61M 15/002* (2014.02); *A61M 15/06* (2013.01); *A61M 2205/8206* (2013.01); *Y02E 60/10* (2013.01)

(58) Field of Classification Search
None
See application file for complete search history.

(56) References Cited

U.S. PATENT DOCUMENTS

2017/0119056 A1 5/2017 Liu

FOREIGN PATENT DOCUMENTS

| CN | 205005906 | 2/2016 |
| CN | 207040881 | 2/2018 |
| | (Continued) | |

OTHER PUBLICATIONS

English machine translation of CN215124368 to Mao published Dec. 14, 2021; 18 pages. (Year: 2021).*

(Continued)

*Primary Examiner* — Linda L Gray
(74) *Attorney, Agent, or Firm* — Nitin Kaushik

(57) ABSTRACT

An electronic cigarette with a suction resistance adjusting function includes a mouthpiece, an electronic cigarette body and an air adjusting mechanism. The air adjusting mechanism includes a microphone starting switch, a flow dividing piece, an air adjusting piece and a bottom cover. The flow dividing piece is provided with a microphone starting air hole and an air suction hole, the microphone starting switch is arranged above the microphone starting air hole. An air adjusting guide groove is provided in the bottom cover, the air adjusting piece extends out of the air adjusting guide groove and is arranged on the bottom cover. A suction resistance is adjustable by blocking air inlet areas of the (Continued)

microphone starting air hole and the air suction hole while stirring the air adjusting piece to move in the air adjusting guide groove.

8 Claims, 5 Drawing Sheets

(56) References Cited

FOREIGN PATENT DOCUMENTS

| | | |
|---|---|---|
| CN | 214677566 | 11/2021 |
| CN | 215124368 | 12/2021 |
| CN | 215684787 | 2/2022 |
| CN | 217407788 | 9/2022 |

OTHER PUBLICATIONS

English machine translation of CN 112656039 to Dong published Apr. 16, 2021; 24 pages. (Year: 2021).*
English machine translation of RU 2601929 C2 to Djubef published Nov. 10, 2016; A24F 40/51; 39 pages. (Year: 2016).*
English machine translation of CN 205005906 U to Chen published Feb. 3, 2016; Y02E60/10; 17 pages. (Year: 2016).*
International Search Report issued in International Application No. PCT/CN2022/140530, mailed Mar. 13, 2023 (6 pages).
Written Opinion of the International Search Authority issued in International Application No. PCT/CN2022/140530, mailed Mar. 13, 2023 (6 pages).

* cited by examiner

ELECTRONIC CIGARETTE WITH SUCTION RESISTANCE ADJUSTING FUNCTION

CROSS-REFERENCE TO RELATED APPLICATIONS

This application is a national stage filing under 35 U.S.C. § 371 of international application number PCT/CN2022/140530, filed Dec. 21, 2022, which claims priority to Chinese patent application No. 202220912044.1, filed Apr. 19, 2022. The contents of these applications are incorporated herein by reference in their entirety.

TECHNICAL FIELD

The disclosure relates to the technical field of electronic cigarettes, and particularly to an electronic cigarette with a suction resistance adjusting function.

BACKGROUND

Electronic cigarette is an electronic product that imitates cigarettes and has the same appearance as cigarettes. The electronic cigarette can vaporize liquid containing nicotine through an atomizer for users to smoke. Generally, the electronic cigarette mainly comprises two parts, i.e., a cigarette rod and a cartridge. The cartridge is internally stored with an atomizing liquid and provided with an atomizer, and the atomizer is powered by a battery in the cigarette rod, so that liquid nicotine in the cartridge can be converted into smoke, so that the user has a feeling similar to smoking when inhaling, realizing "blowing a cloud". Chocolate, mint and other flavors may even be added into a cigarette tube according to personal preference.

At present, the electronic cigarette cartridge on the market generally uses an induction switch to realize the automatic start and stop of the electronic cigarette. When there is an airflow passing through the induction switch, the switch starts an atomization function. However, the induction switch is generally arranged in the suction air channel, resulting in that airflow holes are fixed and the suction resistance is non-adjustable, which cannot meet the different requirements of different people for the suction resistance.

SUMMARY

In order to solve the problems in the prior art, the disclosure provides an electronic cigarette with a suction resistance adjusting function, which solves problems in the prior art that airflow holes are fixed and the suction resistance is non-adjustable, which cannot meet the different requirements of different people for the suction resistance.

The disclosure provides an electronic cigarette with a suction resistance adjusting function, including a mouthpiece, an electronic cigarette body and an air adjusting mechanism, wherein the mouthpiece is arranged at a top end of the electronic cigarette body, and the air adjusting mechanism is arranged at a bottom end of the electronic cigarette body:

the air adjusting mechanism includes a microphone starting switch, a flow dividing piece, an air adjusting piece and a bottom cover which are sequentially arranged from top to bottom, the flow dividing piece is provided with a microphone starting air hole and an air suction hole, the microphone starting air hole and the air suction hole both penetrate through an upper end surface and a lower end surface of the flow dividing piece, and the microphone starting switch is arranged above the microphone starting air hole; and an air adjusting guide groove penetrating through an upper end surface and a lower end surface of the bottom cover is provided in the bottom cover, the air adjusting piece extends out of the air adjusting guide groove and is arranged on the bottom cover, and a suction resistance is adjustable by blocking air inlet areas of the microphone starting air hole and the air suction hole while stirring the air adjusting piece to move in the air adjusting guide groove.

As a further improvement of the disclosure, the flow dividing piece is provided with a clamping block, the bottom cover is provided with a clamping groove matched with the clamping block, and the flow dividing piece is in buckling connection with the bottom cover through the clamping block.

As a further improvement of the disclosure, the air adjusting piece is provided with an air sealing elastic piece, and the air sealing elastic piece is abutted against a lower end surface of the flow dividing piece and configured to improve air tightness between the air adjusting piece and the flow dividing piece.

As a further improvement of the disclosure, the electronic cigarette further includes a microphone elastic piece with an air suction clamping hole, the flow dividing piece is provided with a connecting column extending upward from a position corresponding to the air suction hole, an air suction channel is provided in the connecting column, and communicates with the air suction hole: the air suction clamping hole is consistent to the connecting column in shape: the connecting column is arranged in the air suction clamping hole: a microphone vent hole is provided in the microphone elastic piece corresponding to the microphone starting air hole; and the microphone starting switch is arranged on the microphone elastic piece, and communicates with the microphone starting air hole through the microphone vent hole.

As a further improvement of the disclosure, the air adjusting piece includes a shifting block portion and a sealing portion, the shifting block portion is arranged in the air adjusting guide groove; and ribs are arranged on both sides of an upper surface of the air adjusting guide groove respectively, the ribs are abutted against a lower end surface of the sealing portion and configured to weaken friction force between the air adjusting piece and the bottom cover.

As a further improvement of the disclosure, the microphone elastic piece is provided with a connecting step, the bottom cover is provided with a connecting arm matched with the connecting step, and the microphone elastic piece is in clamping connection with the bottom cover through the connecting step.

As a further improvement of the disclosure, two clamping blocks and two clamping grooves are provided, and the two clamping blocks are symmetrically arranged on both sides of the flow dividing piece.

As a further improvement of the disclosure, at least one microphone starting air hole and at least one air suction hole are arranged in the flow dividing piece at an interval, and a direction in which the at least one microphone starting air hole and the at least one air suction hole are arranged at an interval is consistent to a direction in which the air adjusting piece moves.

As a further improvement of the disclosure, the microphone elastic piece is made of a silica gel material.

As a further improvement of the disclosure, at least one antiskid groove is provided in the air adjusting piece.

Compared with the prior art, the disclosure has the beneficial effects as follows. By adopting the mechanism, the problem of single suction resistance of the electronic cigarette mouthpiece in the prior art can be effectively solved, and the suction resistance of the electronic cigarette can be adjusted steplessly through the air adjusting mechanism, so that maximum autonomous selectivity is provided for the users, and the suction resistance requirements of different users can be met.

BRIEF DESCRIPTION OF THE DRAWINGS

In order to more clearly describe the solutions of the disclosure or in the prior art, the accompanying drawings required to describe the embodiments or the prior art are briefly described below: Apparently, the accompanying drawings described below are some embodiments of this application. Those of ordinary skill in the art may further obtain other accompanying drawings based on these accompanying drawings without inventive effort.

Figure 1:
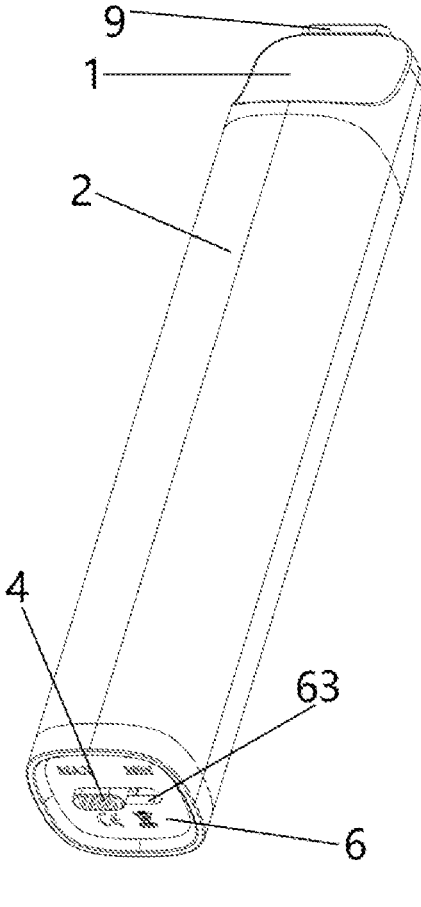
FIG. 1 is a schematic diagram of an overall structure of the disclosure.

Reference numerals: 1—mouthpiece, 2—electronic cigarette housing, 3—microphone starting switch, 4—air adjusting piece, 5—flow dividing piece, 6—bottom cover, 7—microphone elastic piece, 8—air sealing elastic piece, 9—mouthpiece dust-proof plug, 21—E-liquid absorbing cotton, 22—battery, 23—upper silica gel, 24—lower silica gel, 25—E-liquid barrel, 26—glass fiber tube, 27—E-liquid storage cotton, 28—atomization assembly, 41—shifting block portion, 42—sealing portion, 43—antiskid groove, 51—microphone starting air hole, 52—air suction hole, 53—clamping block, 54—second connecting column, 61—clamping groove, 62—connecting arm, 63—air adjusting guide groove, 64—rib, 71—connecting step, and 541—air suction channel.

DETAILED DESCRIPTION

Unless otherwise defined, all the technical and scientific terms used herein have the same meanings as those commonly understood by a person of ordinary skill in the art. Terms used herein in the specification of the disclosure are for the purpose of describing specific embodiments only and are not intended to limit the disclosure. Furthermore, that terms "comprise" and "have" and any variations thereof in the specification and claims as well as the above drawings of the disclosure are intended to cover non-exclusive inclusion. The terms "first", "second" and the like in the specification and claims as well as the above drawings of the disclosure are used to distinguish between different objects, and are not necessarily used to describe a specific sequence.

Reference in the specification to "an embodiment" means that a particular feature, structure, or characteristic described in connection with the embodiment may be included in at least one embodiment of the disclosure. The appearances of the phrase in various places in the specification are not necessarily all referring to the same embodiment, nor are separate or alternative embodiments mutually exclusive of other embodiments. It is to be expressly and implicitly understood by a person of ordinary skill in the art that the embodiments described herein may be combined with other embodiments without conflict.

In order to make a person of ordinary skill in the art better understand the solutions of the disclosure, the technical solutions in the embodiments of the disclosure will be described clearly and completely with the attached drawings.

Figure 2:
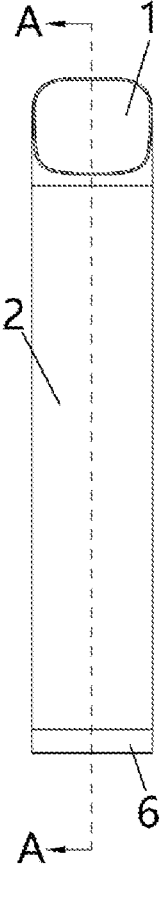
FIG. 2 is a schematic diagram of an overall structure of the disclosure from another viewing angle.
Figure 3:
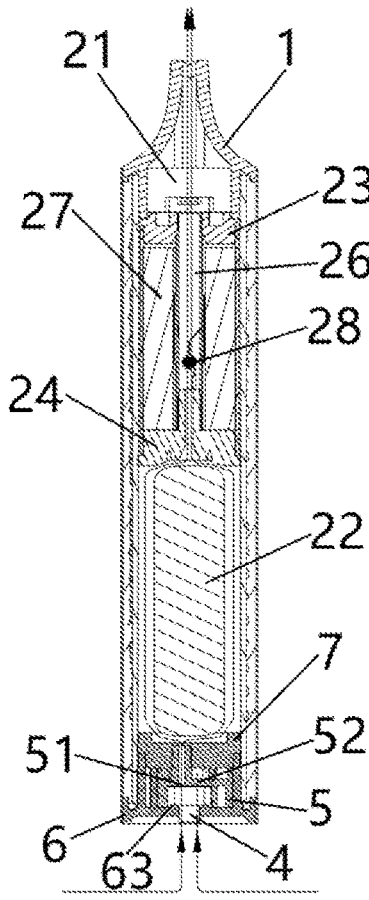
FIG. 3 is a cross-sectional view along A-A in FIG. 2.
Figure 4:
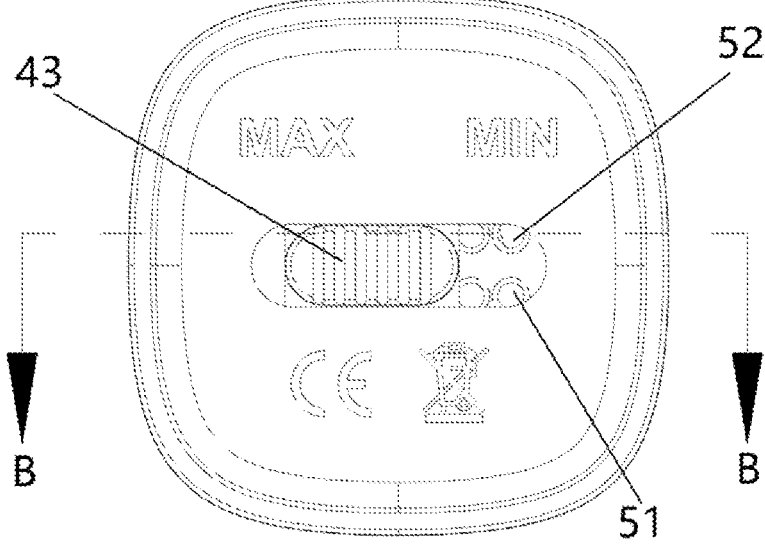
FIG. 4 is a schematic diagram of the present invention from a bottom view.
Figure 5:
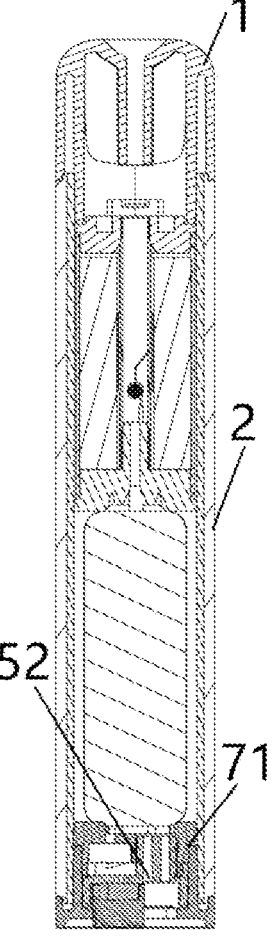
FIG. 5 is a cross-sectional view along B-B in FIG. 4.
Figure 6:
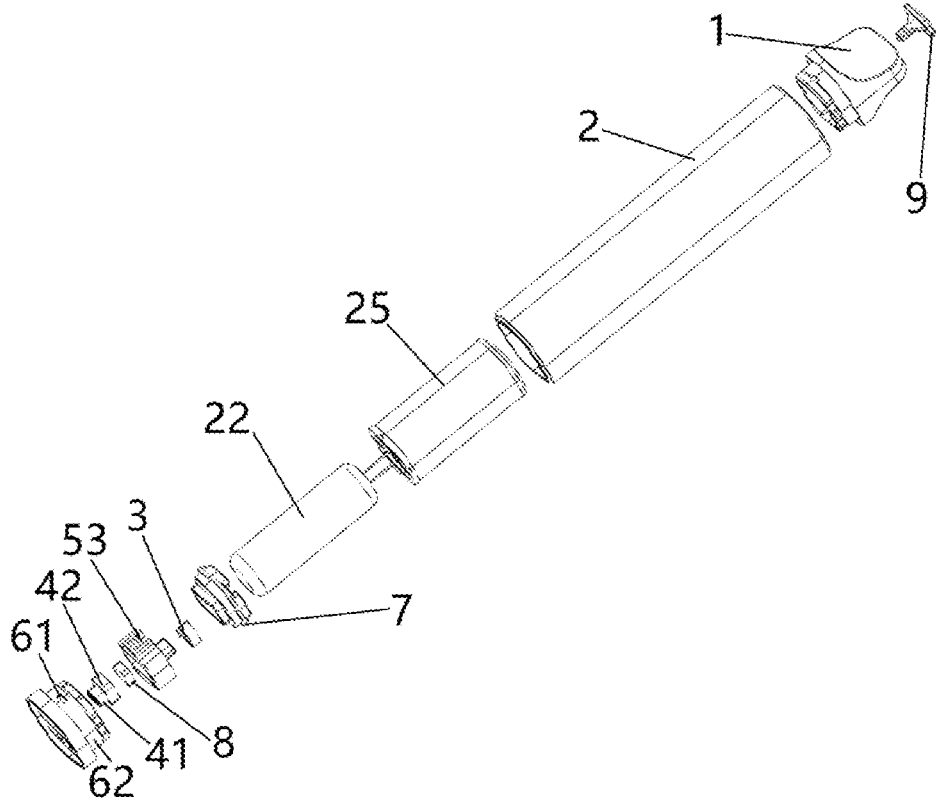
FIG. 6 is a schematic diagram of a decomposition structure of the disclosure.
Figure 7:
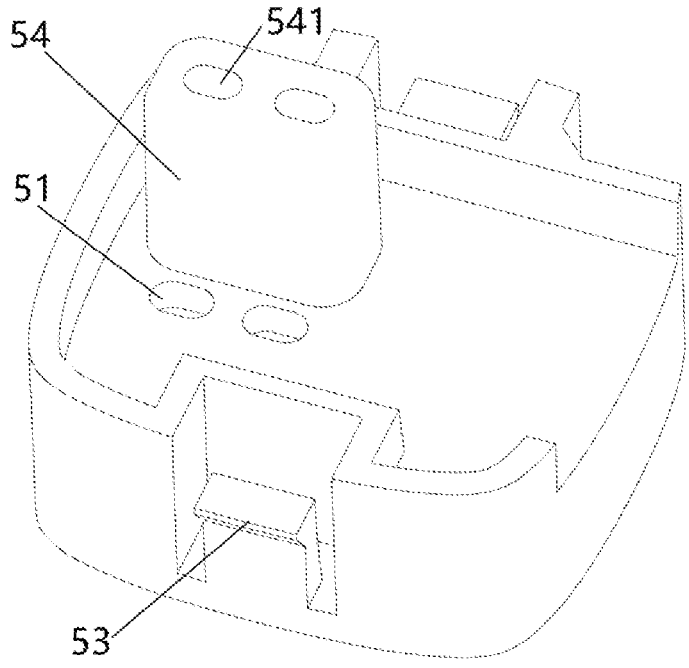
FIG. 7 is a structural schematic diagram of a flow dividing piece.

As shown in FIGS. 1-7, the disclosure provides an electronic cigarette with a suction resistance adjusting function, including a mouthpiece 1, an electronic cigarette body and an air adjusting mechanism. The mouthpiece 1 is arranged at a top end of the electronic cigarette body, and the air adjusting mechanism is arranged at a bottom end of the electronic cigarette body.

The electronic cigarette body includes an electronic cigarette housing 2. An E-liquid absorbing cotton 21, an E-liquid barrel assembly and a battery 22 are arranged in the electronic cigarette housing 2. The E-liquid barrel assembly includes an upper silica gel 23, a lower silica gel 24, an E-liquid barrel 25, a glass fiber tube 26, an atomization assembly 28 and an E-liquid storage cotton 27.

A first through hole penetrating through an upper end surface and a lower end surface of the E-liquid barrel 25 is provided in the E-liquid barrel 25, the glass fiber tube 26 is fixedly arranged in the first through hole, the glass fiber tube 26 has a hollow cylindrical structure, and an airflow channel is arranged in the glass fiber tube 26 . . . .

The atomization assembly 28 is arranged in the airflow channel, and fixedly connected with the airflow channel. Through cooperation of the atomization assembly 28 with the E-liquid barrel 25, the E-liquid is atomized, and then the gaseous E-liquid flows from the airflow channel to the mouthpiece 11 through an airflow.

An E-liquid storage cotton 27 is arranged in the E-liquid barrel 25, the upper silica gel 23 is clamped with a top end of the E-liquid barrel 25, a second through hole penetrating through upper and lower end faces of the upper silica gel 23 is arranged in the upper silica gel 23, the first through hole is fixedly connected with the second through hole, and one end of the glass fiber tube 26 is arranged in the second through hole.

The E-liquid storage cotton 27 in the E-liquid barrel 25 is better sealed and limited by the arrangement of the upper silica gel 23, and the E-liquid barrel 25 is more convenient to assemble and disassemble due to the advantage of the silica gel material.

A first connecting column is arranged at a center position of an upper end surface of the lower silica gel 24, an outer diameter of the first connecting column is matched with the airflow channel, the first connecting column is arranged in the airflow channel, the lower silica gel 24 is clamped with the bottom end of the E-liquid barrel 25, a third through hole penetrating through the first connecting column and the lower silica gel 24 is arranged in the first connecting column, and the third through hole is communicated with the airflow channel.

The E-liquid storage cotton 27 in the E-liquid barrel 25 is better sealed and limited by the arrangement of the lower silica gel 24, and the E-liquid barrel 25 is more convenient to assemble and disassemble due to the advantage of the silica gel material.

A positioning groove for placing the E-liquid absorbing cotton 21 is arranged at the upper end face of the upper silica gel 23, a fourth through hole penetrating through upper and lower end faces of the E-liquid absorbing cotton 21 is arranged in the E-liquid absorbing cotton 21, and the fourth through hole is communicated with the second through hole.

Through the arrangement of the E-liquid absorbing cotton 21, the condensate generated at the mouthpiece 1 can be adsorbed, and a possibility that the condensate flows into the airflow channel can be effectively reduced.

The air adjusting mechanism includes a microphone starting switch 3, a flow dividing piece 5, an air adjusting piece 4 and a bottom cover 6 which are sequentially arranged from top to bottom.

The flow dividing piece 5 is provided with a microphone starting air hole 51 and an air suction hole 52, and the microphone starting air hole 51 and the air suction hole 52 both penetrate through an upper end surface and a lower end surface of the flow dividing piece 5.

The flow dividing piece 5 can effectively separate an airflow for turning on the microphone starting switch 3 from an airflow for air suction, so that mutual interference can be avoided, and the suction resistance of the electronic cigarette can be adjusted.

The flow dividing piece 5 is provided with a clamping block 53, the bottom cover 6 is provided with a clamping groove 61 matched with the clamping block 53, and the flow dividing piece 5 is in buckling connection with the bottom cover 6 through the clamping block 53.

Two clamping blocks 53 and two clamping grooves 61 are provided; and the two clamping blocks 53 are symmetrically arranged on both sides of the flow dividing piece 5. Arrangement of the two clamping blocks 53 makes clamping connection between the flow dividing piece 5 and the bottom cover 6 more stable.

The electronic cigarette with a suction resistance adjusting function further includes a microphone elastic piece 7, an air suction clamping hole is provided in the microphone elastic piece 7. The flow dividing piece 5 is provided with a second connecting column 54 extending upward from a position corresponding to the air suction hole 52, an air suction channel 541 is provided in the second connecting column 54, and communicates with the air suction hole 52. The air suction clamping hole is consistent to the connecting column 54 in shape. The second connecting column 54 is arranged in the air suction clamping hole. A microphone vent hole is provided in the microphone elastic piece 7 corresponding to the microphone starting air hole 51. The microphone starting switch 3 is arranged on the microphone elastic piece 7, and communicates with the microphone starting air hole 51 through the microphone vent hole. Air inlet is achieved through cooperation of the microphone vent hole with the microphone starting air hole 51, to sense on or off of the microphone starting switch 3.

The microphone elastic piece 7 is provided with a connecting step 71, the bottom cover 6 is provided with a connecting arm 62 matched with the connecting step 71, and the microphone elastic piece 7 is in clamping connection with the bottom cover 6 through the connecting step 71.

The microphone elastic piece 7 is made of a silica gel material, and thus clamping connection between the microphone elastic piece 7 and the bottom cover 6 is more stable.

An air adjusting guide groove 63 penetrating through an upper end surface and a lower end surface of the bottom cover 6 is provided in the bottom cover 6. The air adjusting piece 4 includes a shifting block portion 41 and a sealing portion 42, the shifting block portion 41 is arranged in the air adjusting guide groove 63, and partially extends out of the air adjusting guide groove 63, and the sealing portion is abutted against the upper end surface of the bottom cover 6.

The suction resistance may be adjusted by blocking air inlet areas of the microphone starting air hole 51 and the air suction hole 52 while stirring the shifting block portion 41 of the air adjusting piece 4 to make the air adjusting piece 4 move in the air adjusting guide groove 63.

The sealing portion 42 is provided with an air sealing elastic piece 8, and the air sealing elastic piece 8 is abutted against a lower end surface of the flow dividing piece 5. The air sealing elastic piece 8 can further improve the air tightness between the air adjusting piece 4 and the flow dividing piece 5, thereby more accurately adjusting the suction resistance.

Ribs 64 are arranged on both sides of an upper surface of the air adjusting guide groove 63 respectively. The ribs 64 are abutted against a lower end surface of the sealing portion 42, which can weaken friction force between the air adjusting piece 4 and the bottom cover 6.

There are two microphone starting air holes 51 and two air suction holes 52. The microphone starting air holes 51 and the air suction holes 52 are aligned with each other in two rows. The microphone starting air holes 51 are arranged in one row: the air suction holes 52 are arranged in the other row: The two microphone starting air holes 51 are arranged at an interval, and a direction in which the two microphone starting air holes 51 are arranged at an interval is consistent to a direction in which the air adjusting piece 4 moves. The two air suction holes 52 are arranged at an interval, and a direction in which the two air suction holes 52 are arranged at an interval is consistent to the direction in which the air adjusting piece 4 the moves.

At least one antiskid groove 43 is provided in the air adjusting piece 4. The antiskid groove 43 makes a user conveniently stir the air adjusting piece 4 for adjustment.

The electronic cigarette with a suction resistance adjusting function further includes a mouthpiece dust-proof plug 9, which plays a role of dust prevention by effectively preventing dust from entering the mouthpiece 1.

Operations for the electronic cigarette with a suction resistance adjusting function provided by this embodiment are described as follows. When a user smokes with the electronic cigarette, the user inhales from a smoking port of the mouthpiece 1, the airflow passes through the air adjusting guide groove 63, and then passes through the flow dividing piece 5 for flow dividing, and the airflow flows into the microphone starting air holes 51 and the air suction holes 52 respectively.

The airflow from the microphone starting air holes 51 reaches the microphone starting switch 3 above the microphone vent through the microphone vent, and the microphone starting switch 3 is started. The E-liquid barrel 25 supplies E-liquid to the atomization assembly 28, and the battery 22 supplies power to the atomization assembly 28 to atomize the E-liquid.

The airflow from the microphone starting air holes 51 and the air suction holes 52 enters the electronic cigarette, passes through the third through hole, the airflow channel, the second through hole and the fourth through hole in turn, and finally reaches the mouthpiece 11, thus completing the whole smoking process.

When the electronic cigarette is in an initial state, the air adjusting piece 4 does not block the microphone starting air holes 51 and the air suction holes 52. In this case, the suction resistance is the minimum, which is also a critical value for the microphone starting switch 3 to start.

When the suction resistance needs to be adjusted, the shifting block portion 41 is stirred rightward, during which air inlet areas of the microphone starting air holes 51 and the air suction holes 52 are continuously blocked and gradually reduced, followed by a gradual increase in the suction resistance, so that the user can start the microphone starting switch 3 with less suction, which reduces the critical value of the microphone starting switch 3 in a disguised form and adjusts the taste of the mouthpiece 11.

When the shifting block portion 41 is stirred leftward, the air inlet areas of the microphone starting air holes and the air suction holes 52 increase, and the suction resistance decreases, which is easier for the user to smoke the electronic cigarette.

As can be seen from the above, the disclosure has the beneficial effects as follows. By adopting the mechanism, the problem of single suction resistance of the electronic cigarette mouthpiece 1 in the prior art can be effectively solved, and the suction resistance of the electronic cigarette can be adjusted steplessly through the air adjusting mechanism, so that maximum autonomous selectivity is provided for the users, and the suction resistance requirements of different users can be met.

The above describes some embodiments of the disclosure, and is not intended to limit the scope of the disclosure. The scope of the disclosure includes but is not limited to the above embodiments, and all equivalent changes made according to the disclosure are within the protection scope of the disclosure.

What is claimed is:

1. An electronic cigarette with a suction resistance adjusting function, comprising: a mouthpiece, an electronic cigarette body and an air adjusting mechanism:

the air adjusting mechanism comprises a microphone starting switch, a flow dividing component, an air adjusting component and a bottom cover which are sequentially arranged from top to bottom, the flow dividing component is provided with a microphone starting air hole and an air suction hole, the microphone starting air hole and the air suction hole both penetrate through an upper end surface and a lower end surface of the flow dividing component, and the microphone starting switch is arranged above the microphone starting air hole; and an air adjusting guide groove penetrating through an upper end surface and a lower end surface of the bottom cover is provided in the bottom cover, the air adjusting component extends out of the air adjusting guide groove and is arranged on the bottom cover, and a suction resistance is adjustable by blocking air inlet areas of the microphone starting air hole and the air suction hole while stirring the air adjusting component to move in the air adjusting guide groove.

2. The electronic cigarette with a suction resistance adjusting function according to claim 1, wherein the flow dividing component is provided with a clamping block, the bottom cover is provided with a clamping groove matched with the clamping block, and the flow dividing component is in buckling connection with the bottom cover through the clamping block.

3. The electronic cigarette with a suction resistance adjusting function according to claim 2, wherein the air adjusting component is provided with an air sealing elastic component, and the air sealing elastic component is abutted against a lower end surface of the flow dividing component and configured to improve air tightness between the air adjusting component and the flow dividing component.

4. The electronic cigarette with a suction resistance adjusting function according to claim 1, further comprising a microphone elastic component with an air suction clamping hole, the flow dividing component is provided with a connecting column extending upward from a position corresponding to the air suction hole, an air suction channel is provided in the connecting column, and communicates with the air suction hole: the air suction clamping hole is consistent to the connecting column in shape: the connecting column is arranged in the air suction clamping hole: a microphone vent hole is provided in the microphone elastic component corresponding to the microphone starting air hole; and the microphone starting switch is arranged on the microphone elastic component, and communicates with the microphone starting air hole through the microphone vent hole.

5. The electronic cigarette with a suction resistance adjusting function according to claim 3, wherein the air adjusting component comprises a shifting block portion and a sealing portion, the shifting block portion is arranged in the air adjusting guide groove.

6. The electronic cigarette with a suction resistance adjusting function according to claim 3, wherein at least one antiskid groove is provided in the air adjusting component.

7. The electronic cigarette with a suction resistance adjusting function according to claim 4, wherein the microphone elastic component is provided with a connecting step, the bottom cover is provided with a connecting arm matched with the connecting step, and the microphone elastic component is in clamping connection with the bottom cover through the connecting step.

8. The electronic cigarette with a suction resistance adjusting function according to claim 4, wherein the microphone elastic component is made of a silica gel material.

* * * * *